United States Patent [19]

Harada et al.

[11] Patent Number: 5,179,956
[45] Date of Patent: Jan. 19, 1993

[54] CONTACT PRESSURE SENSOR

[75] Inventors: Chikao Harada; Norio Kawamura, both of Nagoya; Ryuji Nakashima, Seto; Arihiro Takahashi, Komaki; Toshimasa Yamazaki, Komaki; Masanobu Yasui, Komaki; Tatsushi Kondo, Urawa, all of Japan

[73] Assignee: Colin Electronics Co., Ltd., Aichi, Japan

[21] Appl. No.: 721,317

[22] Filed: Jun. 26, 1991

[30] Foreign Application Priority Data

Jul. 6, 1990 [JP] Japan .................................. 2-180259
Aug. 22, 1990 [JP] Japan .................................. 2-221642

[51] Int. Cl.$^5$ ........................................... A61B 5/021
[52] U.S. Cl. .................................... 128/672; 128/687; 73/727; 73/754; 73/756; 73/DIG. 4
[58] Field of Search .................... 73/756, 862.67, 754, 73/727; 128/687, 675, 690, 672, 688, 689

[56] References Cited

U.S. PATENT DOCUMENTS

| | | | |
|---|---|---|---|
| 3,817,107 | 6/1974 | Shimada et al. | 73/727 |
| 4,399,707 | 8/1983 | Wamstad | 73/727 |
| 4,423,738 | 1/1984 | Newgard | 128/672 |
| 4,561,477 | 12/1985 | Kawamura et al. | 128/687 |
| 4,665,754 | 5/1987 | Glenn et al. | 73/727 |
| 4,686,764 | 8/1987 | Adams et al. | 73/754 |
| 4,763,098 | 8/1988 | Glenn et al. | 73/727 |
| 4,771,639 | 9/1988 | Saigusa et al. | 73/727 |
| 4,784,152 | 11/1988 | Shihoda et al. | 128/690 |
| 4,830,017 | 5/1989 | Perry et al. | 128/687 |
| 4,839,708 | 6/1989 | Kano et al. | 73/727 |
| 4,901,733 | 2/1990 | Kaida et al. | 128/687 |
| 4,928,700 | 5/1990 | Harada | 128/687 |
| 4,945,762 | 8/1990 | Adamic, Jr. | 73/862.67 |
| 4,947,855 | 8/1990 | Yokoe et al. | 128/690 |
| 4,966,156 | 10/1990 | Perry et al. | 128/687 |
| 4,972,716 | 11/1990 | Tobita et al. | 73/727 |
| 4,987,900 | 1/1991 | Eckerle et al. | 128/687 |
| 5,058,435 | 10/1991 | Terry et al. | 73/727 |

Primary Examiner—Ruth S. Smith
Assistant Examiner—Jeffrey R. Jastrzab
Attorney, Agent, or Firm—Oliff & Berridge

[57] ABSTRACT

A contact pressure sensor including a semiconductor chip having opposite surfaces, at least one pressure sensing element provided in one of the opposite surfaces of the chip, a spacer member supporting the other surface of the chip, a substrate having a surface to which the spacer member is fixed, the one surface of the chip being pressed against an object which produces a pressure, so that the at least one sensing element detects the pressure produced by the object, a first connection terminal provided in the one surface of the chip, a second connection terminal provided in the surface of the substrate, and a flexible flat cable connecting between the first and second connection terminals, the flexible flat cable being bent into two portions one of which extends along a side surface of the spacer member and the other of which extends along the surface of the substrate. The contact pressure sensor may further comprise a light-shading layer covering the one surface of the chip in which the at least one pressure sensing element is provided.

23 Claims, 4 Drawing Sheets

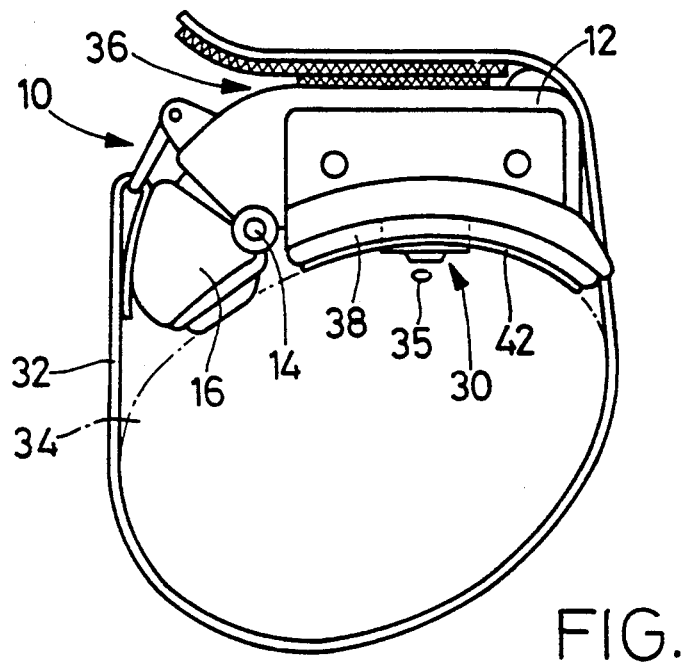
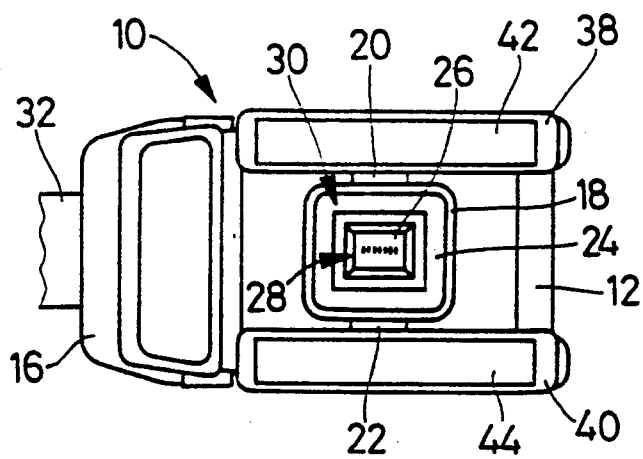

ns a pressure, so as to detect the pressure change
produced between the object and the sensor.

CONTACT PRESSURE SENSOR

BACKGROUND OF THE INVENTION

Field Of The Invention

The present invention relates to a contact pressure sensor which is pressed against an object which produces a pressure, so as to detect the pressure change produced between the object and the sensor.

Related Art Statement

There has been proposed a contact pressure sensor which is adapted to be pressed against an object producing a pressure, so as to detect the pressure change between the object and the sensor. As an example of the contact pressure sensor, U.S. patent application Ser. No. 07/531,055, assigned to the Assignee of the present application, discloses a pulse wave sensor which is pressed against an artery of a subject via body surface, so as to non-invasively detect pressure pulse wave produced from the artery. Oscillatory pressure wave produced from an artery of a subject in synchronism with heartbeat of the subject, i.e., pressure pulse wave reflects not only blood pressure of the subject but also physiological condition of the circulatory system of the subject. For measuring blood pressure and/or making a diagnosis on the circulatory system of a subject, therefore, pressure pulse wave is non-invasively detected by using a contact pressure sensor such as the above indicated pulse wave sensor.

The pulse wave sensor disclosed by the above indicated U.S. patent application is accommodated in a housing which is adapted to be set on a body portion of a subject. The sensor includes (a) a semiconductor chip; (b) a pressure sensing element provided in one surface of the semiconductor chip; a spacer member supporting the other surface of the semiconductor chip; and (d) a substrate to which the spacer member is fixed. The one surface of the semiconductor chip in which surface the pressure sensing element is provided is pressed against an artery of a subject via body surface so that the sensing element detects pressure pulse wave produced from the artery.

In the pulse wave sensor indicated above, a flexible flat cable (FFC) is used to connect between the semiconductor chip and the substrate. The flexible flat cable is constituted by a plurality of foil-based conductor lines and a flexible sheet supporting the conductor lines. The manner of use of the flat cable in the pulse wave sensor is such that the flat cable extends along a diagonal, straight line connecting between bumps (first connection terminals) arranged on the semiconductor chip, and second connection terminals provided on the substrate. Therefore, in the event that the flat cable receives reaction force from the subject because of pressing of the sensor against the body surface of the subject, or in the event that the substrate is warped back due to temperature variation or the flat cable itself shrinks, the flat cable directly transmits to the semiconductor chip stresses due to the reaction force from the subject, the warpage of the substrate, or the shrinkage thereof, because one end of the flat cable is connected to the chip. Thus, strains are produced in the chip, and the accuracy of detection of the pulse wave is lowered.

In addition, the above-indicated pulse wave sensor has no means for shading, against light, the surface of the semiconductor chip in which surface the pressure sensing element is provided. The Applicant has experimental results indicating that the detection of pressure change by the pulse wave sensor is adversely influenced by the light incident to the chip surface supporting the pressure sensing element, resulting in lowering the accuracy of detection of pressure pulse wave. It is speculated that the reason therefor is that the light energy changes mobility of the charge carriers in the pressure sensing element, and thereby changes sensitivity of the pressure sensing element.

SUMMARY OF THE INVENTION

It is therefore a first object of the present invention to provide a contact pressure sensor which effects pressure detection with sufficient accuracy without being influenced by subject's reaction force and/or temperature variation.

It is a second object of the present invention to provide a contact pressure sensor which effects pressure detection with sufficient accuracy without being influenced by light.

The above-indicated first object may be achieved according to a first aspect of the present invention, which provides a contact pressure sensor comprising (a) a semiconductor chip having opposite surfaces, (b) at least one pressure sensing element provided in one of the opposite surfaces of said chip, (c) a spacer member supporting the other surface of the chip, (d) a substrate having a surface to which the spacer member is fixed, the one surface of the chip being pressed against an object which produces a pressure, so that the at least one sensing element detects the pressure produced by the object, (e) a first connection terminal provided in the one surface of the chip, (f) a second connection terminal provided in the surface of the substrate, and (g) a flexible flat cable connecting between the first and second connection terminals, the flexible flat cable being bent into two portions one of which extends along a side surface of the spacer member and the other of which extends along the surface of the substrate.

In the contact pressure sensor according to the first aspect of the invention, the flexible flat cable is bent into two portions, and one of the two portions of the bent flat cable extends along a side surface of the spacer member and the other portion of the bent flat cable extends along the substrate. Therefore, the flat cable is not influenced by the reaction force from a subject to the sensor. In addition, even in the event that the substrate is warped due to temperature variation or the flat cable itself shrinks, substantially no stress is transmitted from the flat cable to the semiconductor chip, since the flat cable is not provided along the diagonal straight line connecting between the bumps (first connection terminals) on the chip and the second connection terminals on the substrate and therefore tensile force is not applied from the flat cable to the chip. Thus, neither subject's reaction force nor temperature variation causes strains in the semiconductor chip. Consequently, the present contact pressure sensor detects pressure variation such as pressure pulse wave with sufficient accuracy.

The above-indicated second object may be achieved according to a second aspect of the present invention, which provides a contact pressure sensor comprising (1) a semiconductor chip having opposite surfaces, (2) at least one pressure sensing element provided in one of the opposite surfaces of the chip, the one surface of the chip being pressed against an object which produces a pressure, so that the at least one sensing element detects the pressure produced by the object, and (c) a light-shading layer covering the one surface of the chip in which the at least one pressure sensing element is provided.

In the contact pressure sensor according to the second aspect of the invention, the surface of the semiconductor chip in which the at least one pressure sensing element is provided, is covered by the light-shading layer. Thus, the semiconductor chip is protected against light. Therefore, the present sensor detects pressure change with sufficient accuracy.

BRIEF DESCRIPTION OF THE DRAWINGS

The above and optional objects, features and advantages of the present invention will be better understood by reading the following detailed description of the presently preferred embodiment of the invention when considered in conjunction with the accompanying drawings, in which:

FIG. 1 is a view showing a pulse wave-detect probe including a pulse wave sensor as a contact pressure sensor of the present invention, the probe being set around a wrist of a subject;

FIG. 2 is a view of the probe of FIG. 1 as viewed from the wrist of the subject;

DETAILED DESCRIPTION OF THE PREFERRED EMBODIMENT

Figure 3:
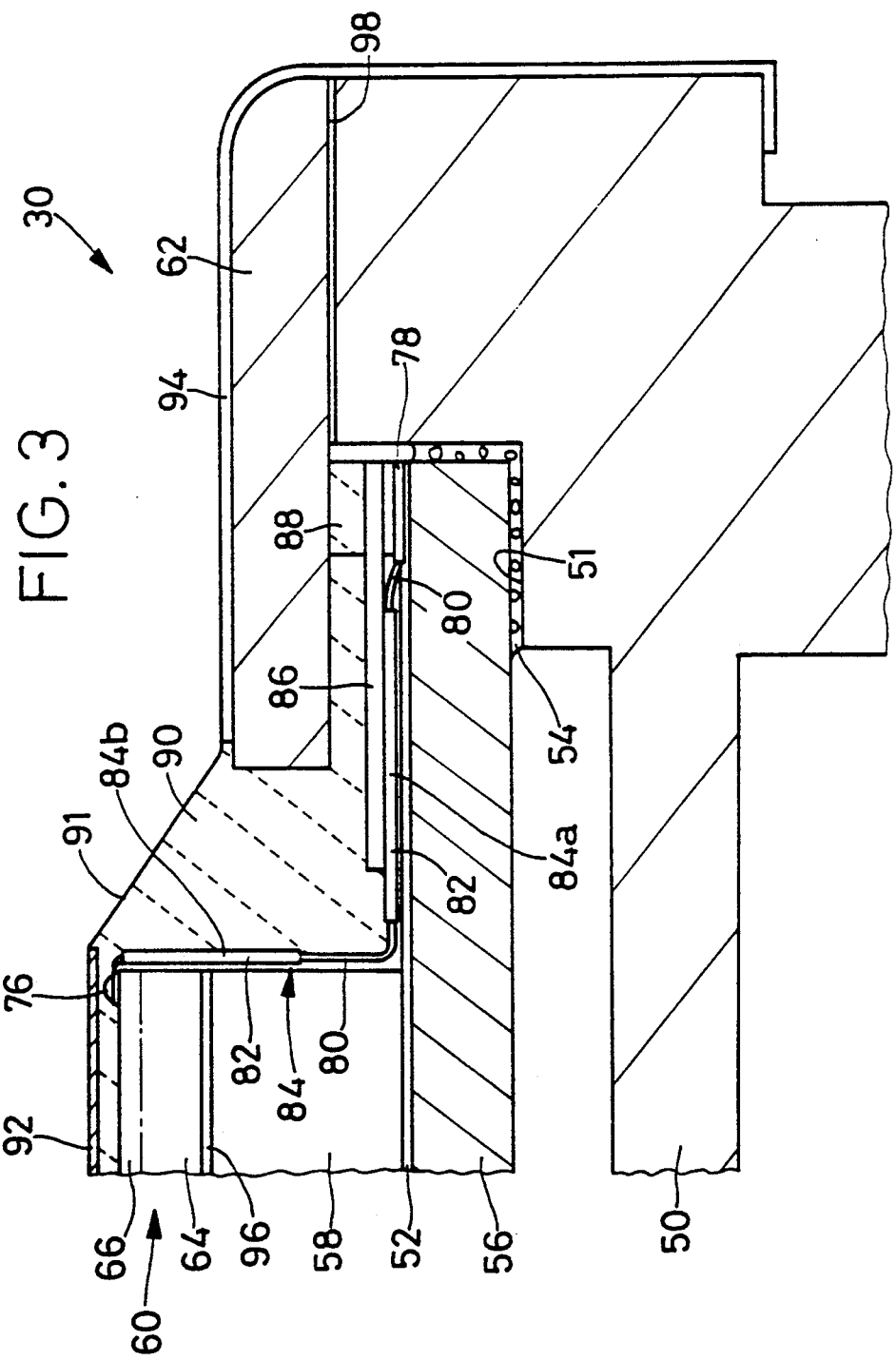
FIG. 3 is an enlarged cross-sectional view of a part of the pulse wave sensor of the probe of FIG. 1.

Referring first to FIGS. 1 and 2, there is shown a pulse wave-detect probe to which the present invention is applied. Reference numeral 10 designates a housing having a container-like configuration. The housing 10 includes a first housing 12 having an open end adapted to contact a wrist 34 of a subject, and a second housing 16 pivotally connected to the first housing 12 by means of a pin 14. In the first housing 12, there is provided a container-like casing 18 having an open end opposed to the wrist 14. The casing 18 has a pair of arms 20, 22 formed integrally therewith, so that the casing 18 is moved rightward and leftward as seen in FIGS. 1 and 2 by means of the arms 20, 22, a pair of guide rods (not shown), and a feed screw (not shown). In the first housing 12, there is also provided a reduction gear unit (not shown) operatively connected to one of opposite ends of the feed screw which one end is nearer to the second housing 16 than the other end. The reduction gear unit is operatively connected via a flexible coupling (not shown) to an output shaft of an electric drive motor (not shown) provided in the second housing 16. This arrangement ensures, irrespective of relative angles of rotation between the first and second housings 12, 16, that the feed screw is driven by the drive motor via the reduction gear unit.

In the casing 18, there is provided an elastic diaphragm 24 which cooperates with an inner wall of the casing 18 to define a pressure chamber (not shown). A pulse wave sensor 30 is secured to one of opposite surfaces of the diaphragm 24, the other surface of which serves for defining the pressure chamber. The pulse wave sensor 30 has a press surface 26 supporting a plurality of pressure sensing elements 28 arranged in an array extending in a direction in which the casing 18 is moved. As fluid pressure in the pressure chamber is increased, the pulse wave sensor 30 is advanced out of the casing 18 and subsequently the first housing 12.

A wrist band 32 is connected at one end thereof to the first housing 12. The housing 10 is set on the wrist 34 in such a manner that the band 32 is wound around the wrist 34 and the other end of the band 32 is fastened to an outer surface of the bottom wall of the first housing 12 with the help of a pair of fastening members 36. In this situation, the array of pressure sensing elements 28 of the pulse wave sensor 30 extends substantially perpendicularly to a radial artery 35 below the skin of the wrist 34. A control device (not shown) controls a pressure regulating device (not shown) to regulate the fluid pressure in the pressure chamber, and at the same time drives the electric motor to move the pulse wave sensor 30 to a position directly above the radial artery 35. By using well-known algorithms, the control device selects the most appropriate one of the pressure sensing elements 28 and determines the most appropriate pressing force (i.e., fluid pressure in the pressure chamber) applied to the pulse wave sensor 30. While the pulse wave sensor 30 is pressed against the wrist 34 with the determined pressing force, the control device receives an electrical signal from the selected pressure sensing element 28. The thus obtained electrical signal is representative of a pressure pulse wave produced from the radial artery 35 in synchronism with heartbeat of the subject and transmitted to the pulse wave sensor 30 (or pressure sensing elements 28). A pair of elongate sponge members 38, 40 are fixed to surfaces of the open end of the first housing 12, so that the first housing 12 contacts the wrist 34 via the sponge members 38, 40. A pair of pressure sensitive adhesive double coated sheets 42, 44 are adhered to the sponge members 38, 40, respectively, so that the first housing 12 is adhered to the wrist 34 with the adhesive force of the double coated sheets 42, 44.

Figure 4:
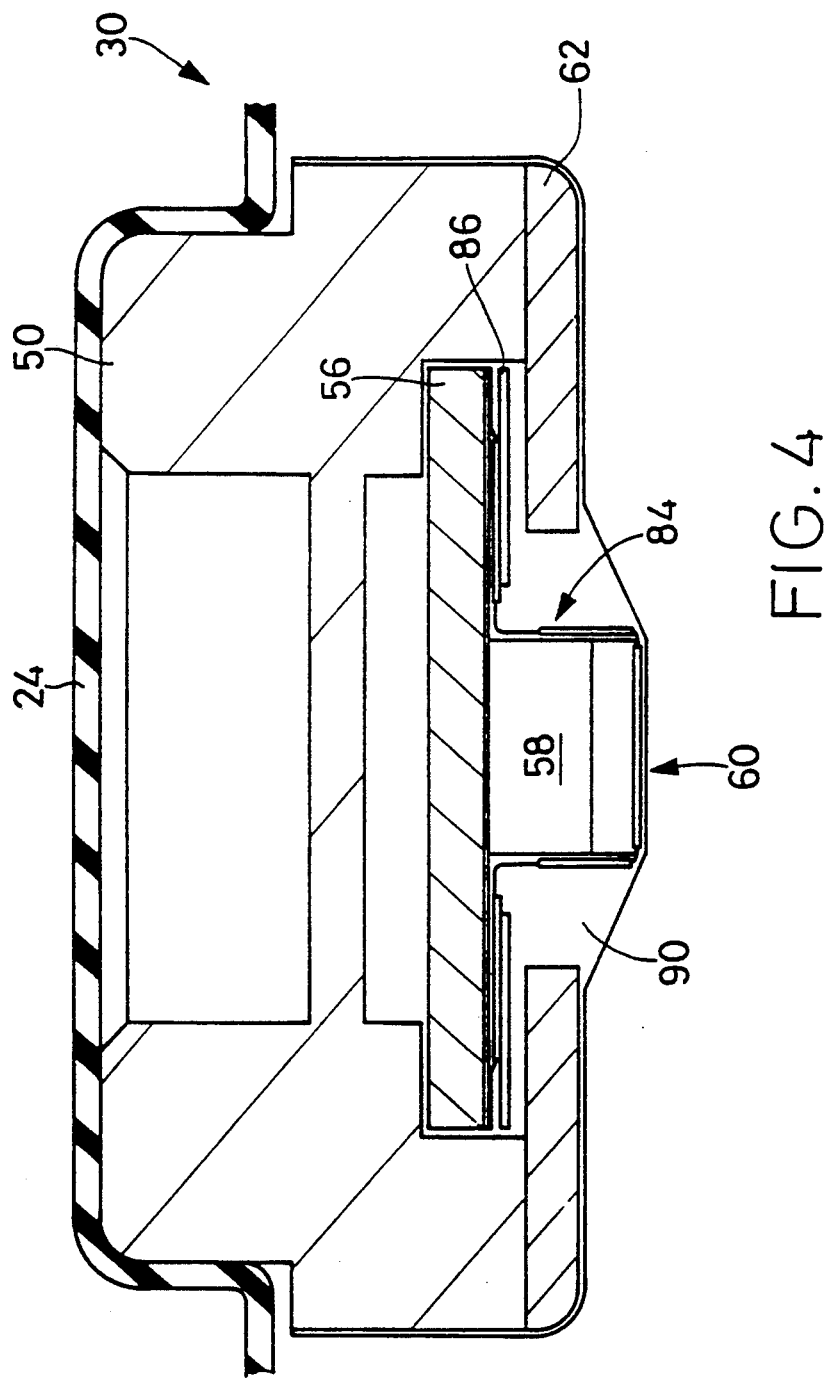
FIG. 4 is an enlarged cross-sectional view of the pulse wave sensor of FIG. 1.

Referring next to FIGS. 3 and 4, there is shown in detail the construction of the pulse wave sensor 30. The pulse wave sensor 30 serves as a contact pressure sensor embodying the present invention. The pulse wave sensor 30 includes a sensor head case 50, a plate member 56, a spacer member 58, a sensor chip 60, and a protection plate 62. The head case 50 is formed of plastics, and is secured to a central portion of the diaphragm 24. The plate member 56 is formed of ceramics, and is accommodated in, and fixed at one of opposite surfaces thereof to, a central recess 51 of the head case 50 via an adhesive layer 54. A conductor pattern 52 is fixed to the other surface of the plate member 56. The spacer member 58 has a rectangular-parallelepiped configuration, and is fixed to a central portion of the plate member 56. The spacer member 58 is formed of aluminum and surface-treated with an electrical insulating material such as plastics and alumite, so that the spacer member 58 acts as an electrical insulator. The sensor chip 60 is adhered to the spacer member 58. The protection plate 62 is formed of metal, and is adhered to the head case 50 for protecting the conductor pattern 52 and its connection terminals 78. The plate member 56 supports a junction circuit serving for electrical connection between the sensor chip 60 and an external main device (not shown). The junction circuit may include a multiplexer, pre-amplifier, regulator, and other active elements, as needed. The plate member 56 also serves for mechanically supporting the sensor chip 60 via the spacer member 58. The plate member 56 serves as a substrate to which the spacer member 56 is fixed.

Figure 5:
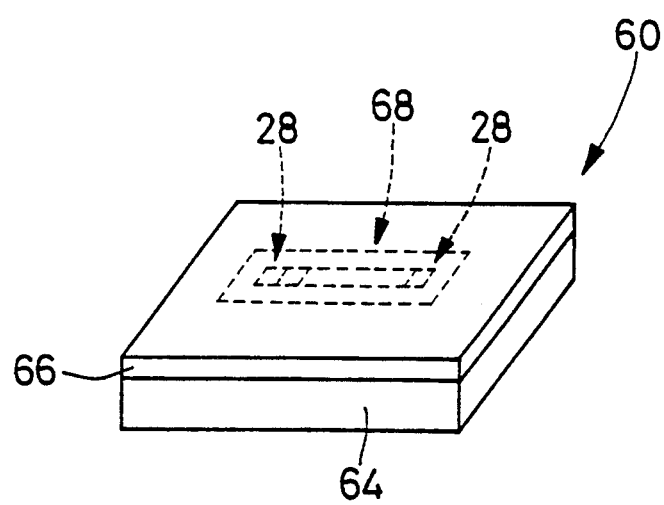
FIG. 5 is a perspective view of a sensor chip employed in the pulse wave sensor of FIGS. 3 and 4.

As shown in FIG. 5, the sensor chip 60 includes a back-up plate 64 and a semiconductor chip 66 adhered to one surface of the back-up plate 64. The back-up plate 64 is formed of a glass having a high rigidity. The semiconductor chip 66 is formed of monocrystalline-silicon plate. The back-up plate 64, which also serves as another spacer member, has a pair of holes (not shown) formed through thickness thereof. Those through-holes cooperate with central holes (not shown) formed through the spacer member and plate member 58, 56 to provide an air passage for applying atmospheric pressure to a surface of the chip 66 which surface is remote from the press surface 26.

The semiconductor chip 66 has a thickness of about 300 microns, and an elongate recess (not shown) is formed in the surface of the chip 66 subjected to atmospheric pressure to thereby provide an elongate diaphragm portion 68 having a thickness of from about several microns to several tens of microns. In the diaphragm portion 68, the pressure sensing elements 28 are provided at regular intervals of distance so that the array of pressure sensing elements 28 extends in a predetermined direction. Each pressure sensing element 28 is constituted by a Wheatstone bridge including four semiconductor resistors formed by a well-known semiconductor manufacturing process such as diffusion or injection of a suitable impurity into the diaphragm portion 68. The arrangement of Wheatstone bridge is described in detail in U.S. patent application Ser. No. 07/630,076 assigned to the Assignee of the present application. Each pressure sensing element 28 detects a contact pressure, namely, pressure change produced at the interface between the press surface 26 and the surface (skin) of the wrist 34, and generates an electrical signal corresponding to strain produced in the diaphragm portion 68 due to the pressure change. This electrical signal, which is representative of the previously described pressure pulse wave, will be referred to as the pulse wave signal. The pulse wave sensor 30 is pressed against the wrist 34 of the subject such that the array of pressure sensing elements 28 is located directly above the radial artery 35 and at the same time extends perpendicularly to the artery 35, so that each pressure sensing element 28 detects the pressure pulse wave and produces a pulse wave signal.

As shown in FIG. 3, a plurality of first connection terminals (bumps) 76 are formed on the other surface of the semiconductor chip 66 which surface is located on the side of the press surface 26. On the other hand, a plurality of second connection terminals 78 are formed on the conductor pattern 52 of the plate member 56. A flexible flat cable 84 connects between the first and second connection terminals 76, 78. The flat cable 84 is constituted by a multiplicity of conductor lines 80 formed of copper foil and spaced apart from each other, and a flexible resin film 82 formed of, for example, polyimide in which the conductor lines 80 are embedded. Two end portions and an intermediate portion of the flat cable 84 are free from the resin film 82, so that the end portions of the conductor lines 80 are electrically connected to the second terminals 78 and the intermediate portion is bent easily. The flat cable 84 is bent at the intermediate portion thereof at about 90 degrees, into two portions one 84a of which extends close along the surface of the plate member 56 and the other portion 84b of which extends close along a side surface of the spacer member 58 vertically from the plate member 56 to the semiconductor chip 66. The exposed end portions of the flat cable 84 are soldered to the first and second connection terminals 76, 78, respectively.

An isolation seal 86 is provided for electrical insulation almost all over the surface of the plate member 56, so that the isolation seal 86 surrounds the spacer member 58 and overlaps a part of the flat cable 84 (84a). An electrical conducting rubber 88 connects between some grounding terminals out of the second connection terminals 78 and the protection plate 62. The surface of the sensor chip 60 on the side of the press surface 26 is covered by a thin layer of silicone rubber 90. The silicone rubber 90 also fills a space provided between the spacer member 58 and the protection plate 62, and forms an inclined surface 91 between the sensor chip 60 and the protection plate 62.

A thin electrical conducting rubber layer 92 is superimposed on the silicone rubber layer 90 above the sensor chip 60 (semiconductor chip 66), so as to provide the press surface 26. The rubber layer 92 is black, and covers the surface of the semiconductor chip 66 in which the pressure sensing elements 28 are provided. The black rubber layer 92 prevents the chip surface supporting the elements 28 from being subjected to light. In the present embodiment, the black rubber layer 92 serves as a light-shading layer for protecting the chip surface with the elements 28 against light. Reference numeral 94 designates a resin isolation seal layer applied to an outer surface of the protection plate 62 for electrical insulation, numeral 96 designates an adhesive layer for adhering the sensor chip 60 and the spacer member 58 to each other, and numeral 98 designates an adhesive layer for adhering the protection plate 62 and the sensor head case 50 to each other. An ultraviolet-curable resin is preferably used for the adhesive layers 96, 98.

In the pulse wave sensor 30 constructed as described above, the flexible flat cable 84 extends vertically from the plate member 56 along the side surface of the spacer member 58. Therefore, the flat cable 84 receives substantially no reaction force from the wrist 34. In addition, even if warpage of the plate member 56 and/or shrinkage of the flat cable 84 itself occur(s) due to temperature variation, no stress is transmitted to the semiconductor chip 66 through the flat cable 84 one end of which is connected to the chip 66, because the flat cable 84 is not provided along an inclined straight line of the smallest length between the first and second connection terminals 76, 78 and accordingly no tensile stress is produced in the flat cable 84. Thus, the semiconductor chip 66 is free from strain due to subject's reaction force and/or temperature variation, and the accuracy of detection of the pressure sensing elements 28 is not adversely influenced by those effects. Consequently, the pulse wave sensor 30 detects pressure pulse wave produced from the subject with sufficient accuracy.

In addition, in the pulse wave sensor 30, the surface of the semiconductor chip 66 in which the pressure sensing elements 28 are provided, is covered by the black, electrical conducting rubber layer 92, which serves as a light-shading layer. The black rubber layer 92 prevents the chip surface having the elements 28 from being exposed to light. Thus, the pressure sensing elements 28 are free from adverse influences due to light, and detect pressure pulse wave with improved accuracy. In this connection, it is noted that conventional pulse wave sensors have no light-shading layer as disclosed above. The silicone rubber layer 90 covering the semiconductor chip 66 is required to be not electrically conducting, and therefore it is a common practice to form the layer 90 of a rubber material having a light color such as white or milk white. The rubber layer 90 of this sort does not function as a light-shading layer, nor contribute to protecting the semiconductor chip 66 against light. Without using the black rubber layer 92, the pressure pulse wave obtained is adversely influenced by the light incident to the semiconductor chip 66, whereby accuracy of detection of the pressure pulse wave is lowered. It is speculated that the reason why the detection of pressure pulse wave is influenced by the light incident to the semiconductor chip 66 is that the light energy is absorbed by electrons in the valence band as one of the electronic energy bands so that the electrons are moved to the conduction band as another of the electronic energy bands, whereby the mobility of the charge carriers in the pressure sensing element 28 is changed and the pressure-to-electricity conversion efficiency of the element 28 (i.e., sensitivity of the element 28) is changed.

Further, the black electrical conducting rubber layer 92 contributes to protecting the pulse wave sensor 30 from influence due to static electricity.

In the illustrated embodiment, the protection plate 62 is grounded through the grounding terminals of the second connection terminals 78. Accordingly, the protection plate 62 serves as a guard ring for preventing the pulse wave sensor 30 from being influenced by high-frequency noise produced by an electric knife, for example.

While the present invention has been described in its preferred embodiment, it is to be understood that the present invention is by no means limited to the details of the illustrated embodiment but may be embodied in various manners.

For example, it is possible to provide a single pressure sensing element in one surface of the semiconductor chip 66, in place of a plurality of elements 28 employed in the illustrated embodiment.

In the illustrated embodiment the two portions 84a, 84b of the flexible flat cable 84 are angled at about 90 degrees. However, even in the event that the two portions 84a, 84b are angled at more than 90 degrees, the pulse wave sensor 30 may enjoy the previously described advantages to an appreciable extent.

Although in the illustrated embodiment the plate member 56 and the conductor pattern 52 fixed to the plate member 56 constitute the substrate for the semiconductor chip 66, it is possible to constitute the substrate by a ceramics plate and a thick conductor wiring provided on one surface of the plate.

The pressure sensing elements 28 are provided at predetermined intervals of distance in the elongate diaphragm portion 68 of the semiconductor chip 66 in the illustrated embodiment. However, it is possible to provide the elements 28 in respective diaphragm portions of independent recesses formed in a semiconductor chip.

The semiconductor chip 66 may be formed by, in place of the monocrystalline-silicon plate used in the illustrated embodiment, a monocrystalline plate of a chemical compound such as gallium arsenide.

While in the illustrated embodiment the pressure sensing element 28 is constituted by a Wheatstone bridge including semiconductor resistors, it is possible to use a pressure sensing diode or transistor for the element 28.

The illustrated pulse wave detect probe is adapted to be set around a wrist so as to detect pressure pulse wave from a radial artery. However, the present invention may be applied to apparatus for detecting pressure pulse wave from a carotid artery or dorsal pedal artery.

It is to be understood that the present invention may be embodied with other changes, improvements and modifications that may occur to those skilled in the art without departing from the scope and spirit of the invention defined in the appended claims.

What is claimed is:

1. A contact pressure sensor comprising:
a semiconductor having opposite surfaces;
at least one pressure sensing element provided in one of said opposite surfaces of said chip;
a spacer member supporting the other surface of said chip, said spacer member having a side surface substantially flush with an edge of said chip;
a substrate having a surface to which said spacer member is fixed;
said one surface of said chip being adapted to be pressed against an object which produces a pressure, so that said at least one sensing element detects said pressure produced by said object;
a first connection terminal provided in said one surface of said chip adapted to be pressed against said object;
a second connection terminal provided in a free portion of said surface of said substrate which portion is free from said spacer member; and
a flexible flat cable connecting between said first and second connection terminals, said flexible flat cable being bent into two portions one of which extends along said side surface of said spacer member and the other of which extends along said free portion of said surface of said substrate.

2. The contact pressure sensor according to claim 1, wherein said flexible flat cable is constituted by a plurality of conductor lines spaced apart from each other and a flexible sheet supporting said conductor lines, said conductor lines being formed of metal foil, said flexible sheet being formed of resin.

3. The contact pressure sensor according to claim 1, wherein said flexible flat cable is bent such that said two portions are angled at about 90 degrees.

4. The contact pressure sensor according to claim 1, further comprising a covering member covering said one surface of said semiconductor chip, said flexible flat cable, said side surface of said spacer member, and said surface of said substrate.

5. The contact pressure sensor according to claim 4, further comprising a black, electrically conducting layer superposed on a portion of the covering member which portion is located directly above said one surface of said chip.

6. The contact pressure sensor according to claim 1, wherein each of said at least one pressure sensing element is constituted by a Wheatstone's bridge including four semiconductor resistors.

7. The contact pressure sensor according to claim 1, further comprising an elastic diaphragm, and a sensor head case fixed at one of opposite surfaces thereof to said diaphragm and having a central recess in the other surface thereof, said substrate being accommodated within, and fixed to, said central recess of said sensor head case.

8. The contact pressure sensor according to claim 1, wherein said substrate includes a plate member formed of ceramics and a conductor pattern fixed to said plate member.

9. The contact pressure sensor according to claim 1, wherein said spacer member is formed of an electrical insulating material.

10. The contact pressure sensor according to claim 1, wherein said semiconductor chip is constituted by a monocrystalline-silicon plate.

11. The contact pressure sensor according to claim 10, further comprising a back-up plate formed of glass to which said semiconductor chip is adhered, said back-up plate having a hole formed therethrough for applying atmospheric pressure to said other surface of said semiconductor chip.

12. The contact pressure sensor according to claim 1, further comprising a casing having a central recess therein;
said substrate being located within said central recess; and an elastic diaphragm coactive between the substrate and the casing for advancing the pressure sensing element with respect to the casing.

13. A contact pressure sensor comprising:
a semiconductor chip having opposite surfaces;
at least one pressure sensing element provided in one of said opposite surfaces of said chip;
said one surface of said chip being pressed against an object which produces a pressure, so that said at least one sensing element detects said pressure produced by said object; and
a light-shading layer covering said one surface of said chip in which said at least one pressure sensing element is provided, said light-shading layer being formed of a black and electrically conducting material.

14. The contact pressure sensor according to claim 13, further comprising a covering member covering said one surface of said semiconductor chip, said light-shading layer being superposed on said covering member.

15. The contact pressure sensor according to claim 14, wherein said covering member comprises a thin rubber layer provided on said one surface of said semiconductor chip.

16. The contact pressure sensor according to claim 13, further comprising a back-up plate to which the other one of said opposite surfaces of said semiconductor chip is adhered.

17. The contact pressure sensor according to claim 13, wherein said semiconductor chip includes an elongate diaphragm portion having a thickness smaller than a thickness of a different portion of said chip, said at least one pressure sensing element being provided in said diaphragm portion.

18. The contact pressure sensor according to claim 17, wherein said at least one pressure sensing element comprises a plurality of pressure sensing elements provided at regular intervals of distance in said elongate diaphragm portion of said semiconductor chip.

19. A contact pressure sensor comprising:
a semiconductor chip having opposite surfaces;
at least one pressure sensing element provided in one of said opposite surfaces of said chip;
said one surface of said chip being pressed against an object which produces a pressure, so that said at least one sensing element detects said pressure produced by said object;
a light-shading layer covering said one surface of said chip in which said at least one pressure sensing element is provided; and
a covering member covering said one surface of said semiconductor chip, said light-shading layer being superimposed on said covering member.

20. The contact pressure sensor according to claim 19, wherein said covering member comprise a thin rubber layer provided on said one surface of said semiconductor chip.

21. The contact pressure sensor according to claim 19, further comprising a back-up plate to which the other one of said opposite surfaces of said semiconductor chip is adhered.

22. The contact pressure sensor according to claim 19, wherein said one surface of said semiconductor chip includes an elongate diaphragm portion having a thickness smaller than a thickness of a different portion of said chip, said at least one pressure sensing element being provided in said diaphragm portion.

23. The contact pressure sensor according to claim 22, wherein said at least one pressure sensing element comprises a plurality of pressure sensing elements provided at regular intervals of distance in said elongate diaphragm portion of said semiconductor chip.

* * * * *